(12) United States Patent
Pujar et al.

(10) Patent No.: US 12,042,764 B2
(45) Date of Patent: Jul. 23, 2024

(54) AIRCRAFT AIR MANAGEMENT SYSTEMS FOR DEACTIVATING CONTAMINANTS

(71) Applicant: Hamilton Sundstrand Corporation, Charlotte, NC (US)

(72) Inventors: Vijay V. Pujar, Rancho Santa Fe, CA (US); Blair A. Smith, South Windsor, CT (US); Claude J. Moreau, Vernon, CT (US); Steven Poteet, Ashland, MA (US); Lance R. Bartosz, Granby, MA (US)

(73) Assignee: HAMILTON SUNDSTRAND CORPORATION, Charlotte, NC (US)

( * ) Notice: Subject to any disclaimer, the term of this patent is extended or adjusted under 35 U.S.C. 154(b) by 0 days.

(21) Appl. No.: 17/313,634

(22) Filed: May 6, 2021

(65) Prior Publication Data

US 2021/0346841 A1   Nov. 11, 2021

Related U.S. Application Data

(60) Provisional application No. 63/028,193, filed on May 21, 2020, provisional application No. 63/022,950, filed on May 11, 2020.

(51) Int. Cl.
*B01D 53/88* (2006.01)
*A61L 9/20* (2006.01)
(Continued)

(52) U.S. Cl.
CPC ............. *B01D 53/885* (2013.01); *A61L 9/20* (2013.01); *B01D 46/0028* (2013.01); *B01D 53/007* (2013.01); *B64D 13/06* (2013.01); *A61L 2209/12* (2013.01); *A61L 2209/134* (2013.01); *B01D 2255/104* (2013.01); *B01D 2255/40* (2013.01); *B01D 2255/50* (2013.01);
(Continued)

(58) Field of Classification Search
None
See application file for complete search history.

(56) References Cited

U.S. PATENT DOCUMENTS 5,840,245 A    11/1998  Coombs et al.
5,933,702 A     8/1999  Goswami
(Continued)

FOREIGN PATENT DOCUMENTS

KR     102050278 B1   12/2019
WO    2007026387 A2    3/2007
(Continued)

OTHER PUBLICATIONS

European Extended Search Report; European Application No. 21172789.6-1101; Date: Oct. 4, 2021; 12 pages.

*Primary Examiner* — Jelitza M Perez
(74) *Attorney, Agent, or Firm* — CANTOR COLBURN LLP

(57) ABSTRACT

An air management system of a vehicle having a conditioned area includes at least one duct defining a flow path for delivering air to the conditioned area and a filter arranged within the at least one duct upstream from the conditioned area. The filter includes a filter media having at least one filter media layer including a plurality of fibers. A coating is applied to at least a portion of the plurality of fibers and the coating is operable to deactivate a microbe arranged in contact with the coating.

16 Claims, 5 Drawing Sheets

(51) Int. Cl.
*B01D 46/00* (2022.01)
*B01D 53/00* (2006.01)
*B64D 13/06* (2006.01)

(52) U.S. Cl.
CPC .. *B01D 2255/802* (2013.01); *B01D 2259/804* (2013.01); *B01D 2279/50* (2013.01); *B01D 2279/65* (2013.01); *B64D 2013/0651* (2013.01)

(56) References Cited

U.S. PATENT DOCUMENTS

| | | |
|---|---|---|
| 7,311,752 B2 | 12/2007 | Tepper et al. |
| 8,303,693 B2 | 11/2012 | Leung |
| 9,266,048 B2 | 2/2016 | Kaddour |
| 2004/0251122 A1 | 12/2004 | Goswami |
| 2008/0031783 A1 | 2/2008 | Briggs et al. |
| 2010/0040655 A1 | 2/2010 | Ren et al. |
| 2013/0327891 A1* | 12/2013 | Zhang ............... B64D 13/08 244/118.5 |
| 2015/0359922 A1* | 12/2015 | Kim .................. A61L 9/20 422/121 |
| 2016/0129432 A1* | 5/2016 | Ozaki ................ A61L 9/205 502/309 |
| 2019/0009912 A1* | 1/2019 | Matsui ............... B64D 13/02 |
| 2020/0122078 A1 | 4/2020 | Trent et al. |

FOREIGN PATENT DOCUMENTS

| | | |
|---|---|---|
| WO | 2011037798 A1 | 3/2011 |
| WO | 2015002324 A1 | 1/2015 |
| WO | 2015111770 A1 | 7/2015 |

\* cited by examiner

US 12,042,764 B2

AIRCRAFT AIR MANAGEMENT SYSTEMS FOR DEACTIVATING CONTAMINANTS

CROSS-REFERENCE TO RELATED APPLICATIONS

This application claims the benefit of U.S. Provisional Application No. 63/028,193 filed May 21, 2020, and U.S. Provisional Application No. 63/022,950 filed May 11, 2021, the disclosures of which are incorporated herein by reference in their entirety.

BACKGROUND

Embodiments of the disclosure relate to an air management system used to provide air to one or more compartments within a vehicle, and more specifically, to a system for sterilizing a portion of the air within the air management system.

Pressurized aircraft have integrated air management systems to provide a pressurized environment, fresh air transfer, recycling, heating, and air conditioning to maintain a comfortable safe environment for occupants for extended periods. Air recycling and replacing stale air requires continuous scrubbing for cleanliness to minimize airborne dust, dirt, odors, fungi and harmful microbes including viruses, spores, and bacteria. This cleaning or scrubbing of the air is typically performed via physical, electrostatic or chemical filtration, and often involve the use of filters and filter media such as a HEPA filter. However, microbes and dirt can accumulate and remain on the filter causing blockage with captured materials which may include active microbes. This blockage requires filters to be cleaned and replaced at periodic intervals. There is also a risk of release of these microbes and potential exposure to harmful microbes when the filters are being cleaned and replaced.

BRIEF SUMMARY

According to an embodiment, an air management system of a vehicle having a conditioned area includes at least one duct defining a flow path for delivering air to the conditioned area and a filter arranged within the at least one duct upstream from the conditioned area. The filter includes a filter media having at least one filter media layer including a plurality of fibers. A coating is applied to at least a portion of the plurality of fibers and the coating is operable to deactivate a microbe arranged in contact with the coating.

In addition to one or more of the features described above, or as an alternative, in further embodiments the coating is applied via one of atomic layer deposition, chemical vapor deposition, physical vapor deposition, dip coating, and spraying.

In addition to one or more of the features described above, or as an alternative, in further embodiments a material of the coating includes copper, silver, and quaternary ammonium compound.

In addition to one or more of the features described above, or as an alternative, in further embodiments the coating is a photocatalytic coating.

In addition to one or more of the features described above, or as an alternative, in further embodiments the photocatalytic coating includes at least one of titanium dioxide, or zinc oxide.

In addition to one or more of the features described above, or as an alternative, in further embodiments the filter media further includes at least one of silver, zeolites or montmorillonite to enhance photocatalytic activity of the photocatalytic coating.

In addition to one or more of the features described above, or as an alternative, in further embodiments comprising a sterilization system including at least one light source, wherein a light emitted by the at least one light source contacts the plurality of fibers.

In addition to one or more of the features described above, or as an alternative, in further embodiments the at least one light source emits a germicidal ultraviolet light.

In addition to one or more of the features described above, or as an alternative, in further embodiments the at least one light source is integrated into the filter.

In addition to one or more of the features described above, or as an alternative, in further embodiments the at least one light source is mounted remotely from the filter.

In addition to one or more of the features described above, or as an alternative, in further embodiments the sterilization system is operational when the air is actively circulating through a portion of the air management system.

In addition to one or more of the features described above, or as an alternative, in further embodiments a first portion of the plurality of fibers within the at least one filter media layer has a first coating material and a second portion of the plurality of fibers within the at least one filter media layer has a second coating material, distinct from the first coating material.

In addition to one or more of the features described above, or as an alternative, in further embodiments the first coating material is a non-photocatalytic material and the second coating material is a photocatalytic material.

In addition to one or more of the features described above, or as an alternative, in further embodiments the first portion of the plurality of fibers and the second portion of the plurality of fibers are arranged within a single filter media layer of the at least one filter media layer.

In addition to one or more of the features described above, or as an alternative, in further embodiments the at least one filter media layer includes a first filter media layer and a second filter media layer, and the first portion of the plurality of fibers is arranged within the first filter media layer and the second portion of the plurality of fibers is arranged within the second filter media layer.

In addition to one or more of the features described above, or as an alternative, in further embodiments comprising an air source, an environmental control system in fluid communication with the air source, a cabin air recirculation sub-system fluidly connected to an outlet of the conditioned area, an air mixing unit connected to the environmental control system and to the cabin air recirculation sub-system, and an air distribution system extending from the air mixing unit to one or more vents associated with the conditioned area.

In addition to one or more of the features described above, or as an alternative, in further embodiments the at least one duct is a portion of the cabin air recirculation sub-system.

In addition to one or more of the features described above, or as an alternative, in further embodiments the conditioned area is a cabin of an aircraft.

In addition to one or more of the features described above, or as an alternative, in further embodiments the air is cabin recirculation air provided from an outlet of the conditioned area.

In addition to one or more of the features described above, or as an alternative, in further embodiments comprising a sterilization system including at least one light source operable to emit a light over the plurality of fibers, wherein the sterilization system is operational when the air is actively circulating through a portion of the air management system.

According to another embodiment, a method of forming a filter capable of neutralizing microbes includes providing a filter media including a plurality of fibers and applying a coating to one or more fibers of the plurality of fibers via atomic layer deposition. The coating has a thickness less than an average pore size of the filter media and the coating is operable to deactivate a microbe arranged in contact with the coating.

In addition to one or more of the features described above, or as an alternative, in further embodiments the coating is a photocatalytic material.

In addition to one or more of the features described above, or as an alternative, in further embodiments comprising applying at least one of silver, zeolites and montmorillonite to enhance photocatalytic activity of the photocatalytic material.

In addition to one or more of the features described above, or as an alternative, in further embodiments comprising sterilizing the filter media by emitting a light that contacts the plurality of fibers.

In addition to one or more of the features described above, or as an alternative, in further embodiments the light is a germicidal ultraviolet light.

In addition to one or more of the features described above, or as an alternative, in further embodiments comprising installing the filter within an air management system of a vehicle having a conditioned area.

In addition to one or more of the features described above, or as an alternative, in further embodiments the vehicle is an aircraft.

In addition to one or more of the features described above, or as an alternative, in further embodiments installing the filter within an air management system of a vehicle further comprises installing the filter within a cabin air recirculation system of the air management system.

BRIEF DESCRIPTION OF THE DRAWINGS

The following descriptions should not be considered limiting in any way. With reference to the accompanying drawings, like elements are numbered alike.

DETAILED DESCRIPTION

A detailed description of one or more embodiments of the disclosed apparatus and method are presented herein by way of exemplification and not limitation with reference to the Figures.

Figure 1:
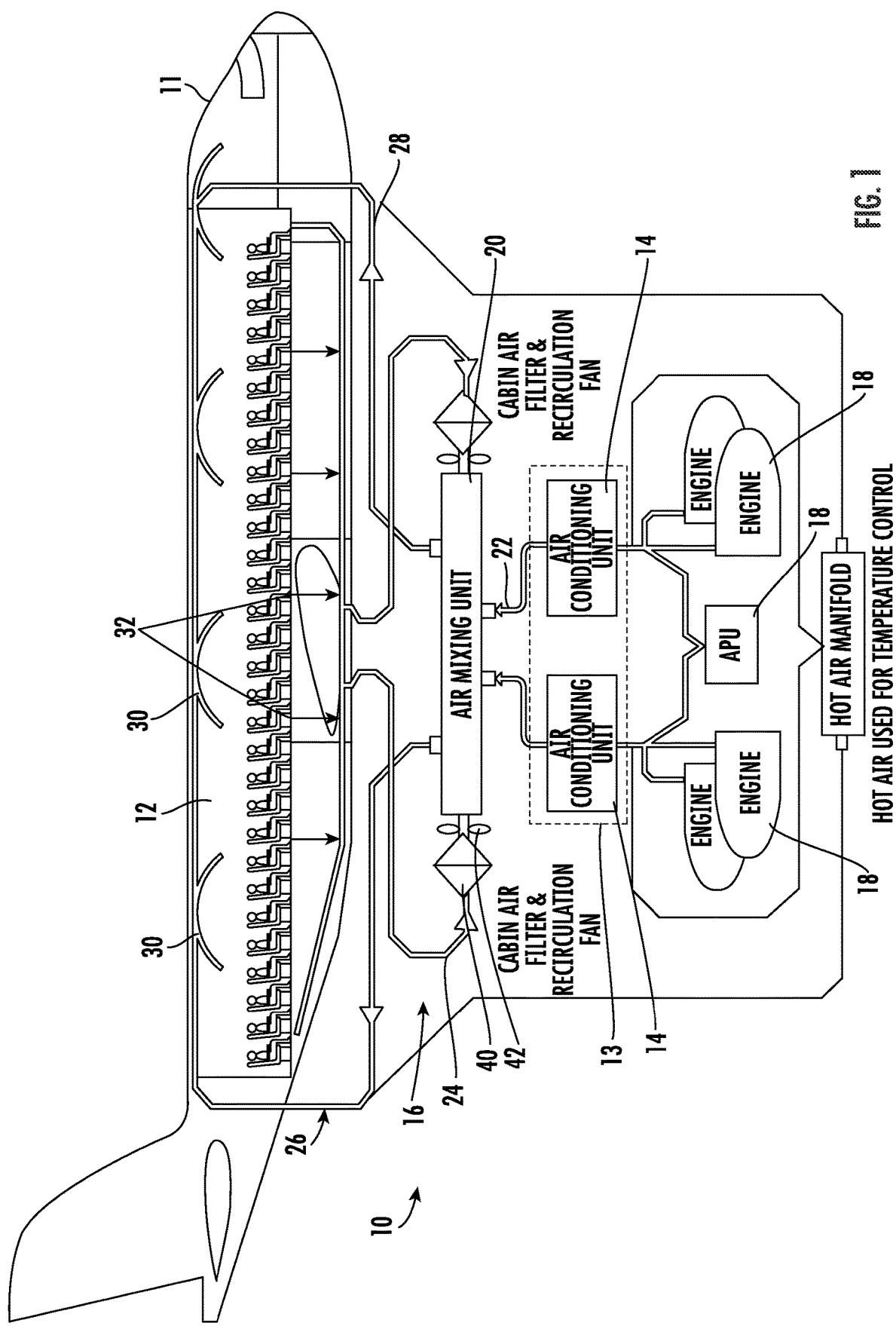
FIG. 1 is a schematic diagram of an air management system of an aircraft.

With reference now to FIG. 1, a schematic of an example of an air management system 10 to control the air of a vehicle, such as an aircraft 11 is illustrated. The aircraft 11 includes a conditioned area or cabin 12 that the air management system 10 controls. The cabin 12 may be configured to house people, cargo, and the like therein. The air management system 10 provides conditioned air to, and removes used or contaminated air from, the cabin 12. The air management system 10 includes an environmental control system 13 having at least one air conditioning unit or pack 14, and a cabin air recirculation sub-system 16. While the air management system 10 is illustrated and described herein with reference to an aircraft 11, it should be understood that the systems and techniques discussed herein may be used for a variety of air management systems 10. For example, the cabin 12 may be replaced with any closed volume to be conditioned. As such, systems described herein may be used with ship air management systems, such as submarines and cruise liners for example, personnel carrier air management systems, bus, trolley, train, or subway air management systems, or any other air management system that requires a continual supply of conditioned air.

As shown in the FIG. 1, a medium, such as air for example, is provided from one or more sources 18 to the air management system 10. Examples of suitable sources 18 include but are not limited to an engine of the aircraft 11 and an auxiliary power unit of the aircraft 11. The medium output from these sources 18 is provided to the one or more air conditioning units 14 of the environmental control system 13. Within these air conditioning units 14, the medium is conditioned. This conditioning includes altering one or more of a pressure, temperature, humidity, or flow rate of the medium based on an operating condition of the aircraft. The medium output or discharged from the one or more air conditioning units 14 of the environmental control system 13 may be used maintain a target range of pressures, temperatures, and/or humidity within the cabin 12.

The medium discharged from the air conditioning units 14 is provided to an air mixing unit or mixing manifold 20 via one or more outlet ducts 22. Similarly, at least one duct 24 of the cabin air recirculation sub-system 16 extends from the cabin 12 to the air mixing unit 20 to deliver air exhausted from the cabin 12 to the air mixing unit 20. Within the air mixing unit 20, the cabin recirculating air is mixed with the medium output from the one or more air conditioning units 14 to achieve a mixed medium having one or more desired parameters, such as temperature, pressure, and humidity for example.

In an embodiment, the mixed medium is delivered to the cabin 12 from the air mixing unit 20 via an air distribution system 26 including one or more conduits 28. As shown, the mixed medium may be delivered to the cabin 12 and cockpit via a ventilation system arranged near a ceiling of the cabin 12. In some embodiments, the mixed medium typically circulates from the top of the cabin 12 toward the floor, and is distributed to a plurality of individual vents 30 of the ventilation system spaced laterally between the front and rear of the cabin 12. It should be understood that the air management system 10 illustrated and described herein is intended as an example only, and that any suitable air management system is within the scope of the disclosure.

Figure 2:
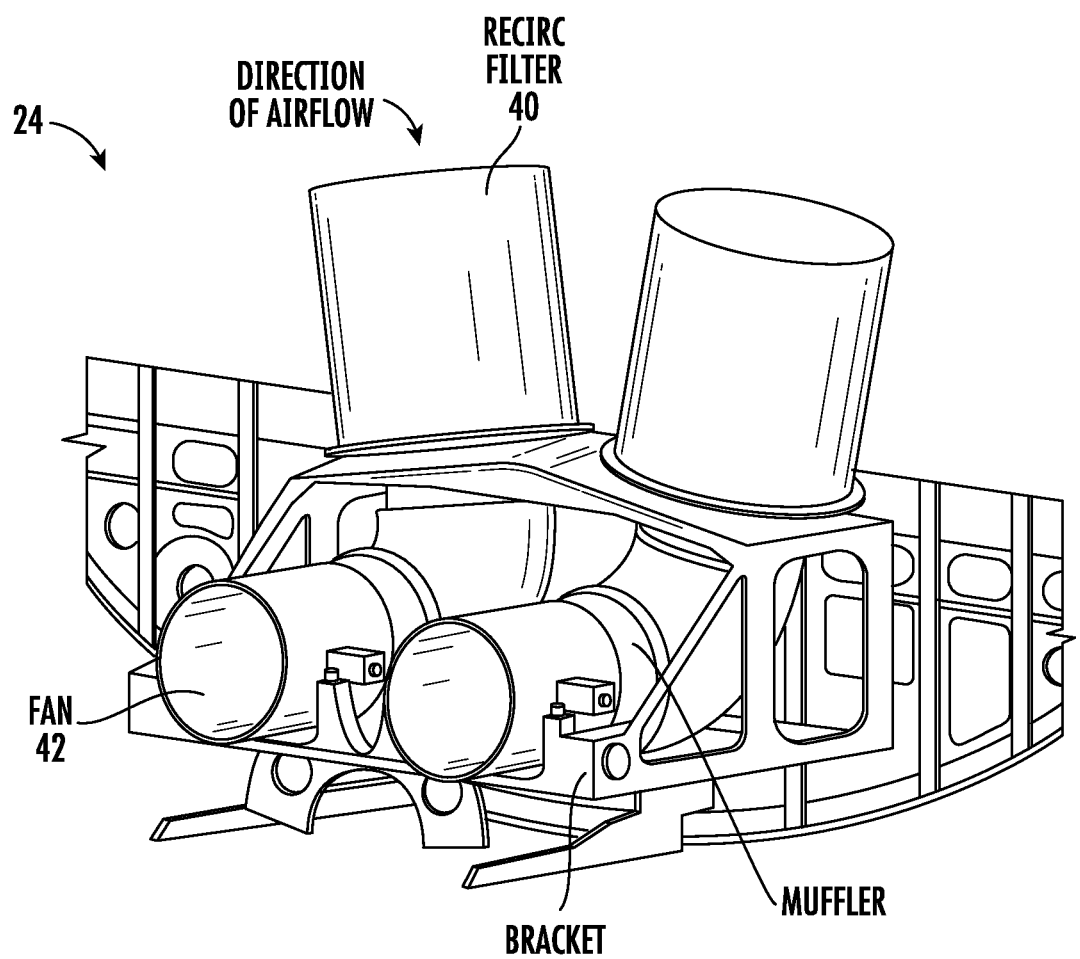
FIG. 2 is a perspective view of a portion of a duct of an air management system according to an embodiment.

With reference now to FIG. 2, an example of a portion of the cabin air recirculation sub-system within the air management system 10 is shown in more detail. In the illustrated, non-limiting embodiment, a portion of the duct 24 of the cabin air recirculation sub-system 16 and fluidly connects one or more outlets 32 (see FIG. 1) of the cabin 12 to the air mixing unit 20. Mounted within the duct is a filter 40 configured to remove harmful microbes such as bacteria, viruses, spores, fungi and particulate matter from the cabin recirculation air provided from the outlets 32 in the cabin 12 as it flows through the filter 40. Although the filter 40 is shown as being arranged adjacent a downstream end of the duct, such as directly upstream from an interface between the duct and the air mixing unit, a filter arranged at any location within the duct is contemplated herein. Further, although the filter 40 is illustrated as having a circular configuration in FIG. 2, and a rectangular configuration in FIG. 3, it should be understood that a filter 40 having any configuration is within the scope of the disclosure. In an embodiment, the filter 40 comprises a HEPA-type filter. However, any suitable filter, or combination of multiple filters is within the scope of the disclosure. Further, in an embodiment, the duct 24 includes a recirculation fan 42 to establish an overpressure that is used to drive the flow of the recirculating cabin air through the filter 40 and to the air mixing unit 20. However, embodiments of a portion of a cabin air recirculation sub-system 16 that do not include a fan such that air flow through the duct 24 is driven by another source or by pressure for example, are also contemplated herein.

Figure 3:
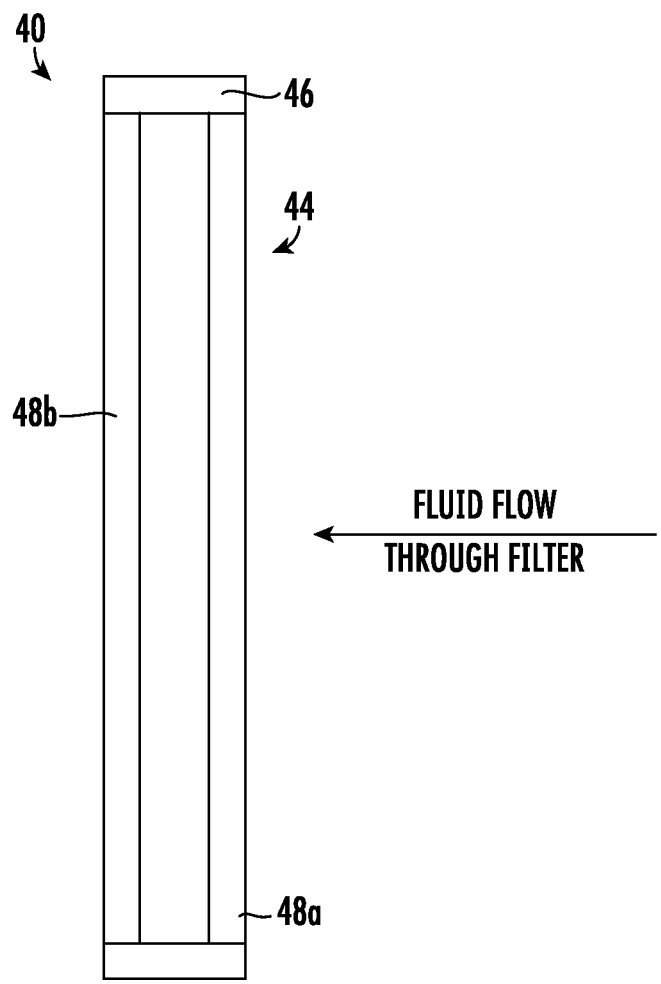
FIG. 3 is a cross-sectional view a filter according to an embodiment.
Figure 4:
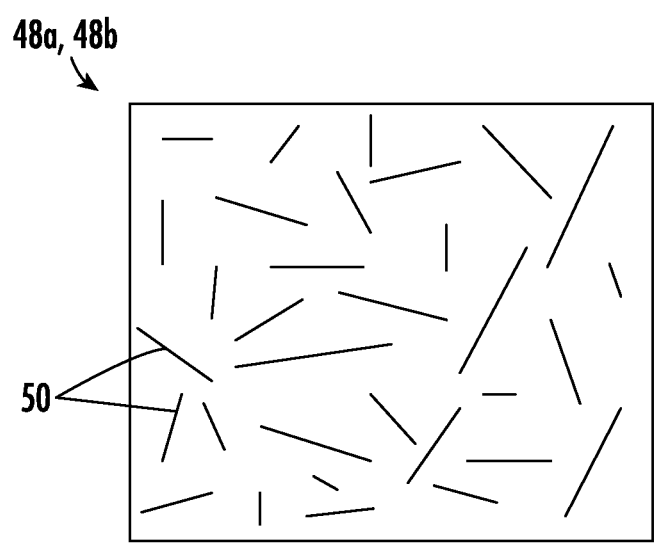
FIG. 4 is a plan view of a layer of filter media of the filter of FIG. 3 according to an embodiment.

An example of a filter, such as the HEPA filter 40 of the cabin air recirculation sub-system 16, is illustrated in more detail in FIGS. 3 and 4. As shown, the filter 40 typically includes a filter media 44 and a frame or other structure 46 for mounting the filter media 44 at a desired position within a duct, such as duct 24. The filter media 44 may include one or more layers. For example, in the illustrated, non-limiting embodiment of FIG. 3, the filter media 44 includes at least a first layer 48a and a second layer 48b stacked in overlapping arrangement relative to a direction of fluid flow through the filter media 44. However, a filter media 44 having a single layer or alternatively, three, four, five, or more layers is also within the scope of the disclosure.

The one or more layers 48 of filter media 44 typically consist of a plurality of fibers 50, such as glass fibers for example. However, any suitable type of fibers 50, including carbon fibers and metal fibers for example, are contemplated herein. The fibers 50 may be randomly oriented, or alternatively, may be unidirectionally oriented at any suitable angle within the layer. In embodiments including a plurality of layers, the orientation of the fibers 50 may vary between adjacent layers 48. The fibers 50 of the one or more layers of filter media 44 cooperate to form a tortuous fluid flow path that traps or adsorbs fine particles and microbes between adjacent fibers 50 or on the exposed surface of the fibers 50. In an existing filter, these particles, which include bacteria and viruses, typically remain trapped at the filter media 44 until the filter media 44 is cleaned and/or replaced.

In an embodiment, the fibers 50 integrated into the one or more layers of filter media 44 are coated with a material capable of deactivating or neutralizing any microbes, including bacteria and viruses, that contact the material. Examples of such materials include, but are not limited to copper (Cu), and silver (Ag). Further, in an embodiment, the coating material is a photocatalytic material, which as described herein is configured to deactivate or neutralize a microbe upon contact when the coating material is activated by a light having a specific wavelength. Any photocatalytic material exhibiting a suitable band gap which can be excited by incident light to create positive holes and electrons of sufficient energy to create oxidizing and reducing radicals may be suitable. Examples of photocatalytic materials include, but are not limited to, titanium dioxide ($TiO_2$) and doped titanium dioxide, Zinc Oxide (ZnO), for example.

In an embodiment, the photocatalytic activity of the photocatalytic coating may be enhanced by combination with other materials. Examples of such materials include but are not limited to, silver, zeolites and layered silicate materials such as montmorillonite. For example, montomorlilonite may help to absorb light and enhance the effectiveness of titanium dioxide in creating oxidizing and reducing radicals that help to deactivate microbes.

The fibers 50 within a layer of the filter media 44 may be coated with a single coating material, or alternatively, may be coated with a variety of coating materials including a combination of non-photocatalytic materials and photocatalytic materials. For example, a first portion of the fibers 50 within a layer of the filter media 44 may be coated with copper or silver, a second portion of the fibers 50 within the same layer of the filter media 44 may be coated with titanium dioxide. Further, a third portion of the fibers 50 within the same layer of the filter media 44 may be coated with quaternary ammonium compound, such as quaternary ammonium silane monomers or copolymers for example.

To avoid blocking or plugging of the pores of the filter media 44, the total layered thickness of the coating applied to the fibers 50 may be less than the average pore size of the filter media 44. The average pore size as used herein refers to the effective size of the particles that the filter is able to capture. Further, in an embodiment, each layer of the coating material is a thin layer having a thickness less than the average pore size of the filter media 44. Accordingly, the one or more layers of coating material may each have a thickness less than or equal to 300 nm, 200 nm, or even 100 nm.

In an embodiment, vapor deposition, such as atomic layer deposition for example, is used to form one or more of the layers of the coating applied to the fibers 50. Atomic layer deposition is a molecular layer-by-layer approach that results in a buildup where each layer has a thickness measured in angstroms ($10^{-10}$). Because the thickness of each layer that can be achieved via atomic layer deposition is so small, such a process may be particularly beneficial when forming a coating have a thickness less than a micron ($10^{-6}$). However, it should be understood that any suitable method for applying the coating material to the fibers 50 is contemplated herein. Examples of such methods include, but are not limited to chemical vapor deposition, and physical vapor deposition, dip coating, spraying or painting. With these various coating methods, the individual fibers 50, or the fibers as woven to form a layer, may be coated before or after being assembled to form the filter media 44 or cartridge, with the latter being more economical. Further, application of a coating material via vapor deposition, such as atomic layer deposition for example, permits non-line-of-sight coating because a molecular layer of the coating may be formed anywhere the vapor makes contact. By coating the fibers 50 using a non-line of sight coating method, the coating may be applied after both the formation and installation of the filter, since gases can penetrate the tiny pores of the fiber filter media.

In an embodiment, the fibers 50 may be coated by more than one method. For example, a portion of the fibers 50 may be coated with photocatalytic material by atomic layer deposition, while a second portion of fibers 50 may be coated with quaternary ammonium silane compound by dip coating in a solution comprising acetone and a quaternary ammonium silane copolymer and drying in air. In embodiments where different coating methods are used, the coating materials being applied may be the same or different.

In embodiments where the coating includes a photocatalytic coating, the filter media 44 disclosed herein may be decontaminated or cleaned by emitting a light having a desired wavelength over the filter media 44. The light energizes the coating material or acts as a catalyst, causing the coating to neutralize or deactivate any microbes in contact therewith. This emission of light may be performed manually, or alternatively, may be performed automatically, such as by a sterilization system 52 integrated into the duct 24, adjacent the filter 40.

Figure 5:
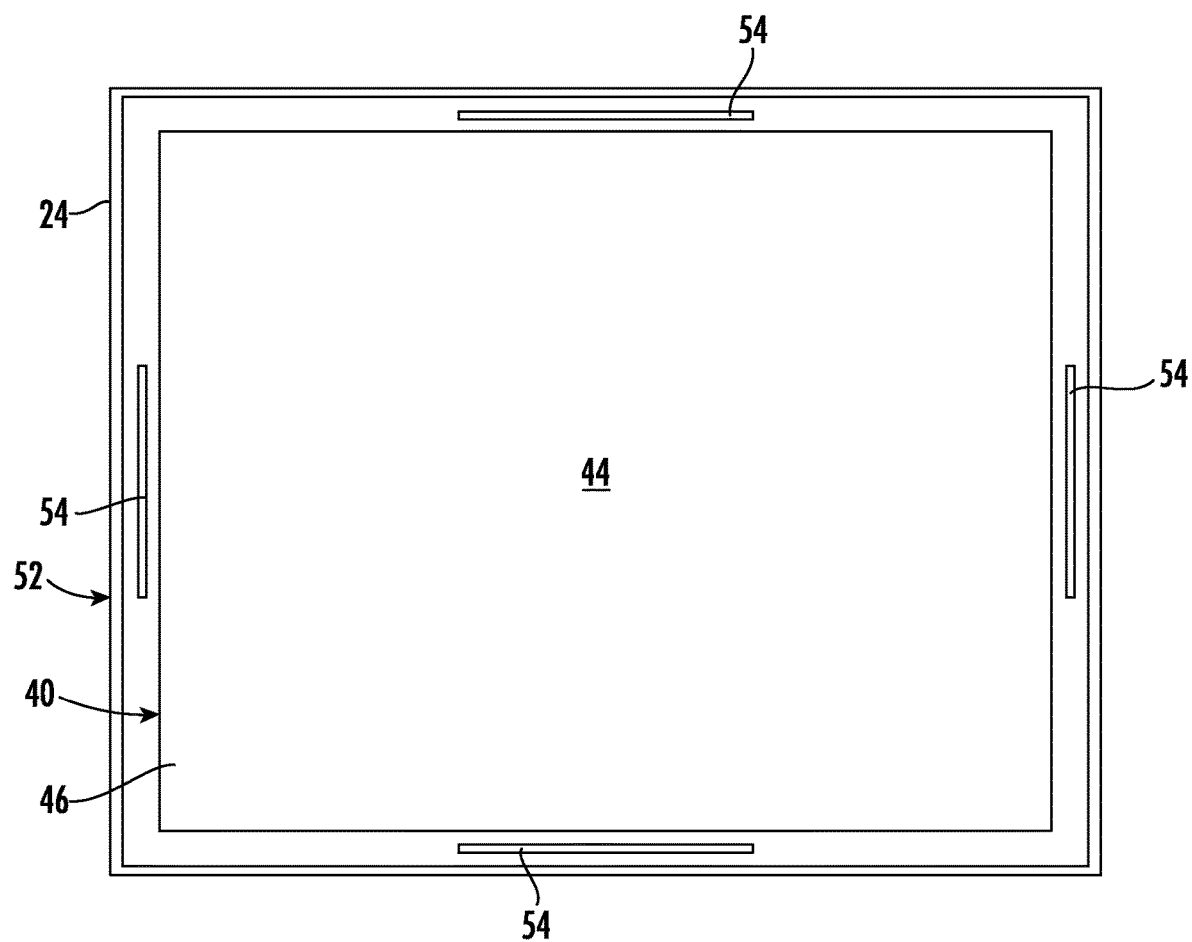
FIG. 5 is a front view of a filter mounted within a duct including a sterilization system according to an embodiment.
Figure 6:
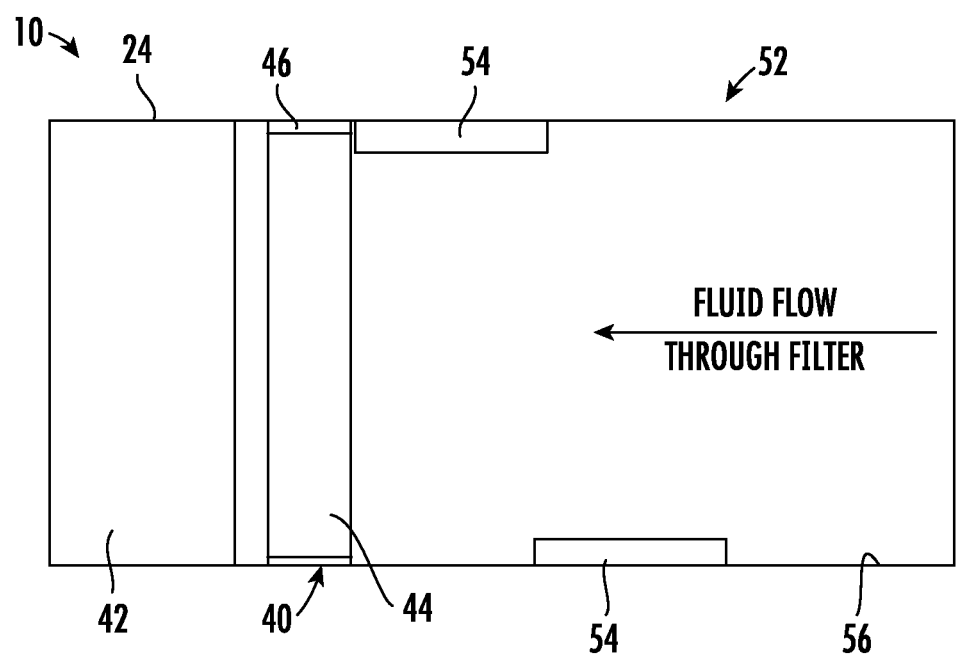
FIG. 6 is a cross-sectional view of a portion of a duct of an air management system including a sterilization system according to an embodiment.

With reference now to FIGS. 5 and 6, the sterilization system 52 includes at least one light source 54 capable of emitting a light having a wavelength suitable to perform germicidal irradiation. In an embodiment, the light source 54 is operable to emit a germicidal ultraviolet light, such as having a wavelength between about 200 and about 280 nanometers, also known as "UV-C." However, a light having another wavelength, such as visible light for example, is also within the scope of the disclosure. Additionally, a light source 54 having any configuration, such as an individual bulb, a light strip having a plurality of bulbs or light emitting diodes, or another type of emitter, is contemplated herein. The light sources 54 of the sterilization system 52 may be operable intermittently, or in an embodiment, are operable whenever air is actively circulating through a portion of the air management system 10.

In an embodiment, one or more light sources 54 are mounted such that the light emitted therefrom projects over at least a portion, and in some embodiments, over the entire filter 40, and specifically, the filter media 44. The light sources 54 may be integrated into a portion of the filter 40 itself, such as the frame 46 for example, as shown in FIG. 5. Alternatively, or in addition, the one or more light sources 54 may be mounted remotely from the filter, such as within the duct 24 at a position adjacent the filter 40 or at a position axially offset from the filter 40. As a result of the light emitted by the one or more light sources 54 over the filter media 44, any viruses or bacteria present on the filter 40, such as trapped by the fibers 50 in the filter media 44 itself, are killed or neutralized.

One or more interior surfaces 56 of the duct 24 or other surfaces within the region illuminated by the one or more light sources 54 may have a reflective or mirrored surface or coating to facilitate increased distribution of the germicidal light throughout the duct 24. A reflective or mirrored surface or coating as described herein may include, but is not limited to, one or more of aluminum, gold, chrome, nickel, titanium, copper, silver, copper oxide, titanium dioxide, zinc oxide, or another suitable shiny material or polished surface. Further, such a coating may be applied via any suitable method, such as via a spray, dip, wipe, vapor deposition, plating, or other known method. In an embodiment, the coating material is applied via vapor deposition, such as via atomic layer deposition for example. Application of a coating material via atomic layer deposition permits non-line-of-sight coating because a molecular layer of various germicidal chemical compounds may be formed anywhere the vapor makes contact.

A filter media 44 having fibers 50 coated with a material capable of neutralizing microbes, such as a photocatalytic material for example, has an improved effectiveness in deactivating harmful microbes. As a result, the need to replace the filter cartridge may be reduced, and further, the potential exposure to harmful microbes during such replacement is reduced if not eliminated.

The term "about" is intended to include the degree of error associated with measurement of the particular quantity based upon the equipment available at the time of filing the application.

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

While the present disclosure has been described with reference to an exemplary embodiment or embodiments, it will be understood by those skilled in the art that various changes may be made and equivalents may be substituted for elements thereof without departing from the scope of the present disclosure. In addition, many modifications may be made to adapt a particular situation or material to the teachings of the present disclosure without departing from the essential scope thereof. Therefore, it is intended that the present disclosure not be limited to the particular embodiment disclosed as the best mode contemplated for carrying out this present disclosure, but that the present disclosure will include all embodiments falling within the scope of the claims.

What is claimed is:

1. An air management system of an aircraft having a conditioned area comprising: an air mixing unit;
   at least one duct defining a flow path for delivering air to the conditioned area, the at least one duct extending between the conditioned area and the air mixing unit; and
   a filter arranged within the at least one duct upstream from the conditioned area, the filter including a frame and a filter media mounted within the frame, the filter media having a plurality of filter media layers stacked in an overlapping arrangement such that the plurality of filter media layers are arranged in series relative to a flow of the air, each of the plurality of filter media layers including a plurality of fibers; and
   at least one coating is applied to at least a portion of the plurality of fibers, the coating being operable to deactivate a microbe arranged in contact with the coating;
   wherein a first portion of the plurality of fibers within a filter media layer of the plurality of filter media layers has a first coating material and a second portion of the plurality of fibers within the filter media layer of the plurality of filter media layers has a second coating material;
   wherein the conditioned area is a cabin of the aircraft.

2. The air management system of claim 1, wherein a material of the coating includes copper, silver, and quaternary ammonium compound.

3. The air management system of claim 1, wherein the coating is a photocatalytic coating.

4. The air management system of claim 3, wherein the first portion of the plurality of fibers further includes at least one of silver, zeolites, or montmorillonite to enhance photocatalytic activity of the photocatalytic coating.

5. The air management system of claim 1, further comprising a sterilization system including at least one light source, wherein a light emitted by the at least one light source contacts the plurality of fibers.

6. The air management system of claim 5, wherein the at least one light source emits a germicidal ultraviolet light.

7. The air management system of claim 5, wherein the sterilization system is operational when the air is actively circulating through a portion of the air management system.

8. The air management system of claim 1, wherein the first coating material is a non-photocatalytic material and the second coating material is a photocatalytic material.

9. The air management system of claim 1, further comprising:
an air source;
an environmental control system in fluid communication with the air source;
a cabin air recirculation sub-system fluidly connected to an outlet of the conditioned area; and
an air distribution system extending from the air mixing unit to one or more vents associated with the conditioned area;
wherein the air mixing unit is connected to the environmental control system and to the cabin air recirculation sub-system.

10. The air management system of claim 9, wherein the at least one duct is a portion of the cabin air recirculation sub-system.

11. A method of forming a filter capable of neutralizing microbes comprising:
providing a filter having a frame and a filter media mounted to the frame, the filter media including a plurality of filter media layers stacked in an overlapping arrangement such that the plurality of filter media layers are arranged in series relative to a flow of the air, each of the plurality of filter media layers including a plurality of fibers; and
applying a first coating to a first portion of the plurality of fibers of a filter media layer of the plurality of filter media layers via atomic layer deposition and applying a second coating to a second portion of the plurality of fibers of the filter media layer of the plurality of filter media layers, wherein at least one of the first coating and the second coating has a thickness less than an average pore size of the filter media and at least one of the first coating and the second coating is operable to deactivate a microbe arranged in contact therewith;
installing the filter within an air management system of an aircraft having a conditioned area including a cabin, the filter being arranged within a duct defining a flow path for delivering air to the conditioned area, wherein the duct extends between an outlet of the cabin and an air mixing unit.

12. The method of claim 11, wherein the first coating is a photocatalytic material.

13. The method of claim 12, further comprising applying at least one of silver, zeolites, and montmorillonite to the first portion of the plurality of fibers to enhance photocatalytic activity of the photocatalytic material.

14. The method of claim 11, further comprising sterilizing the filter media by emitting a light that contacts the plurality of fibers.

15. The method of claim 14, wherein the light is a germicidal ultraviolet light.

16. The method of claim 11, wherein installing the filter within an air management system of the aircraft further comprises installing the filter within a cabin air recirculation system of the air management system.

* * * * *